United States Patent
Lacroix et al.

(10) Patent No.: US 7,893,255 B2
(45) Date of Patent: Feb. 22, 2011

(54) PROCESS FOR THE SYNTHESIS OF LAURYLLACTAM (L12) BY GAS PHASE CATALYTIC REARRANGEMENT OF CYCLODODECANONE OXIME

(75) Inventors: Eric Lacroix, Amberieux d'Azergues (FR); Serge Hub, Villeurbanne (FR); Wolfgang Holderich, Frankenthal (DE); Wilm Eickelberg, Liederbach (DE); Francois Fajula, Teyran (FR); Francesco DiRenzo, Montpellier (FR); Markus Brandhorst, Lyons (FR)

(73) Assignee: Arkema France, Colombes (FR)

( * ) Notice: Subject to any disclaimer, the term of this patent is extended or adjusted under 35 U.S.C. 154(b) by 374 days.

(21) Appl. No.: 11/472,024

(22) Filed: Jun. 21, 2006

(65) Prior Publication Data

US 2008/0214836 A1     Sep. 4, 2008

Related U.S. Application Data

(60) Provisional application No. 60/719,842, filed on Sep. 23, 2005.

(30) Foreign Application Priority Data

Jun. 21, 2005  (FR) .................................. 05 06263

(51) Int. Cl.
*C07D 225/02* (2006.01)
*B01J 29/06* (2006.01)

(52) U.S. Cl. ........................................ 540/464; 502/64
(58) Field of Classification Search .................. 502/64; 540/464

See application file for complete search history.

(56) References Cited

U.S. PATENT DOCUMENTS

| | | | |
|---|---|---|---|
| 3,586,668 A | 6/1971 | Immel et al. | |
| 6,051,706 A | 4/2000 | Holderich et al. | |
| 6,071,844 A | 6/2000 | Holderich et al. | |
| 2004/0054169 A1 | 3/2004 | Tsunoda et al. | |

FOREIGN PATENT DOCUMENTS

| | | |
|---|---|---|
| EP | 1 193 251 | 9/2001 |
| JP | 2003/321443 | 11/2003 |
| JP | 2004/352623 | 12/2004 |
| WO | WO 2004/037785 | * 5/2004 |
| WO | WO 2004037785 | 5/2004 |

OTHER PUBLICATIONS

Climent et al. "Novel delaminated zeolites are more active acid catalysts than conventional zeolites and mesoporous Al/MCM-41 for the synthesis of fine chemicals" Studies in Surface Sciences and Catalysts, 2001, vol. 135, pp. 3719-3726.*
Climent et al., "Studies in Surface Sciences and Catalysis"—2001, 135, pp. 3719-3726.

* cited by examiner

*Primary Examiner*—Joseph R Kosack
(74) *Attorney, Agent, or Firm*—Thomas F. Roland

(57) ABSTRACT

The present invention relates to a process for the preparation of lauryllactam in which a Beckmann rearrangement of cyclododecanone oxime is carried out. Said process is carried out in the gas phase at a temperature of between 180 and 450° C. in the presence of a microporous material having a three-dimensional inorganic main structure composed of tetrahedra connected via a common edge, called zeolite.

21 Claims, 1 Drawing Sheet

Figure 1: Lifetime
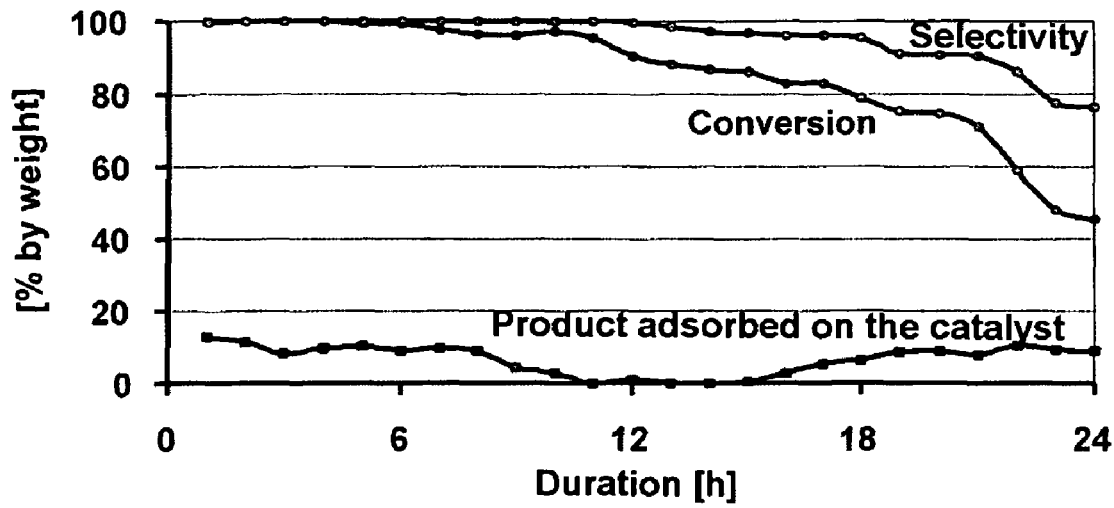
Figure 2: Regeneration of the catalyst
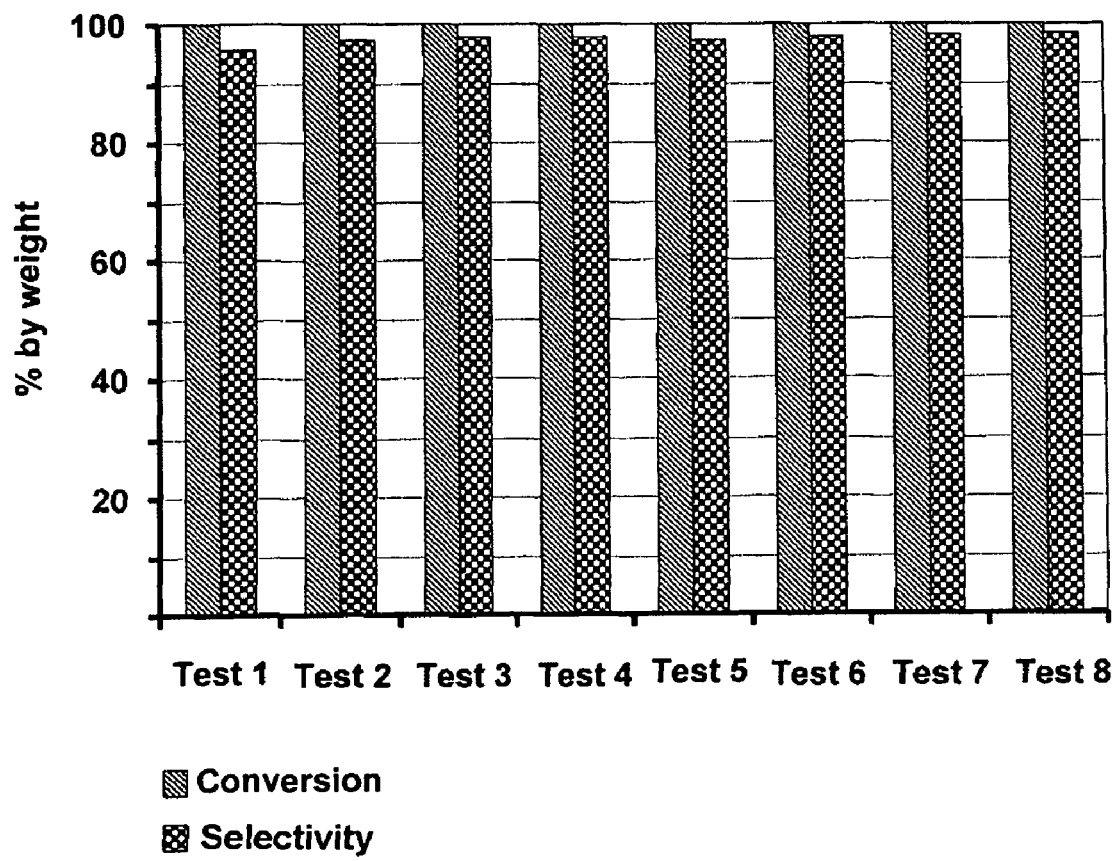

PROCESS FOR THE SYNTHESIS OF LAURYLLACTAM (L12) BY GAS PHASE CATALYTIC REARRANGEMENT OF CYCLODODECANONE OXIME

This application claims benefit, under U.S.C. §119(a) of French National Application Number 05.06263, filed Jun. 21, 2005; and also claims benefit, under U.S.C. §119(e) of U.S. provisional application 60/719,842, filed Sep. 23, 2005.

FIELD OF THE INVENTION

The present invention relates to a process for the synthesis of lauryllactam (L12) by catalytic rearrangement of cyclododecanone oxime. This rearrangement is carried out in the gas phase in the presence of a catalyst of zeolite type.

BACKGROUND OF THE INVENTION

Caprolactam and lauryllactam are respectively the precursors of polyamides 6 and 12. Industrially, the conventional process for synthesizing lactams from cyclic ketoximes is based on a reaction in an acidic medium, for example sulfuric acid. Large amounts of acid are necessary and the recovery of the lactam necessitates the neutralization of the medium by a base. Consequently, in addition to the disadvantages related to the use of acid, the latter has to be neutralized after the reaction. It therefore cannot be recycled and results in a significant by-production of undesirable discharges (by-production of 3 to 5 tonnes of ammonium sulfate per tonne of lactam when sulfuric acid is used and when the medium is neutralized with ammonia). Various processes, in particular using heterogeneous catalysis, have been envisaged in order to avoid this by-production of products which cannot be recovered in value.

In a recent paper published in Studies in Surface Sciences and Catalysis (2001, 135, 3719-3726), Maria Climent et al. describe the synthesis of delaminated zeolites and their applications in organic synthesis. They describe in particular the use of these solids for the Beckmann rearrangement in a batchwise liquid-phase process. Dealuminated β zeolite is mentioned among the solids given as examples; the conversion and the selectivity obtained with this zeolite for the rearrangement of cyclododecanone oxime to L12 are 16 and 98% respectively. The selectivity is thus high; in contrast, the conversion remains low with this type of catalyst. Furthermore, there is no information on the gas-phase Beckmann rearrangement.

The Beckmann rearrangement has also been operated by heterogeneous catalysis in the gas phase, in particular for the synthesis of caprolactam. Specifically, processes have been developed although these are compounds with high boiling points (206-210° C. for cyclohexanone oxime and 139° C./12 mmHg for caprolactam). Apart from looking for the good catalyst which will result in a high catalytic activity, the major difficulty is the stability of the catalyst, which rapidly deactivates as a result of adsorption/decomposition of the organic compounds. In the case of the rearrangement of cyclododecanone oxime, the organic compounds are even heavier than those of the series comprising six carbon atoms. This is why, even if a few short-duration tests are described in the literature, an industrial process appears to be difficult to envisage due to the difficulty in maintaining the catalytic activity.

U.S. Pat. No. 3,586,668 discloses the synthesis of lactam by gas-phase rearrangement over catalytic systems consisting of a mixture of boron trioxide or of boric acid and of carbon which is highly dispersed (particle size of less than 0.1 mm) and in the presence of water. This patent discloses and exemplifies in particular the synthesis of caprolactam; however, the final example (Example 8) describes the synthesis of lauryllactam over a catalyst having a particle size of between 1 and 2 mm. The test described in this example is of short duration (5 hours 15 minutes) and, although the content of L12 in the final mixture is mentioned (86%), it is not possible to deduce therefrom the reaction yield since the weight of product obtained is not indicated. Furthermore, no information on the stability and the lifetime of the catalyst is given.

The problems encountered during a gas-phase Beckmann rearrangement over a heterogeneous catalyst are mentioned in Patent Application JP 48012754 A (registration No. 44-76676 of 7 Oct. 1969 on behalf of Asahi Chemical Industry). Inter alia, the inventors bring up the problem of very rapid deactivation of the catalyst related to the thermal decomposition and the polymerization of the organic compounds on the solid. To overcome these difficulties, in particular for cyclododecanone oxime, the inventors recommend the use of catalysts composed of boric acid deposited on a porous support, such as diatoms. Example 1 of this patent describes the rearrangement of cyclododecanone oxime over a catalyst of this type. Although repeated 30 times, the test is of short duration (5 minutes). It is mentioned that the conversion is stable if the temperature is 300° C.; in contrast, no information is given with regard to the selectivity for or the yield of L12.

The synthesis of caprolactam by gas-phase heterogeneous catalysis over β zeolites or zeolites of MFI type is claimed in U.S. Pat. No. 6,051,706 and U.S. Pat. No. 6,071,844. Out of concern for improving the performances of the catalysts, in particular for reducing their deactivation, on the one hand, the cyclohexanone oxime is dissolved in ethanol and, on the other hand, the catalysts are modified (use of zeolites comprising boron and treatment of the MFIs in order to remove all or part of the central metal atoms). Despite this, the inventors were driven to work on the regeneration of the catalyst in the presence of air or of nitrogen. The synthesis of L12 is not mentioned in these patents since they are restricted to the synthesis of caprolactam.

Patent Application WO 2004/037785 discloses the catalytic rearrangement of cyclododecanone oxime to give lauryllactam (L12) either (i) in the gas phase or (ii) in the liquid phase in the presence of a catalyst which is a monolaminar silicate with an acidic nature. This catalyst is prepared by delamination of the precursor of a zeolite with a laminar structure; this is therefore not a zeolite.

The prior art has described the catalytic rearrangement of cyclododecanone oxime to give lauryllactam (L12) either (i) in the gas phase over catalysts which are not zeolites (FR 1 562 298 and JP 48012754 A) or (ii) in the liquid phase over zeolites (Studies in Surface Sciences and Catalysis (2001, 135, 3719-3726)). A zeolite is defined as a microporous material having a three-dimensional inorganic main structure composed of tetrahedra connected via a common edge (fully linked corner-sharing tetrahedra); see in particular "Nomenclature of structural and compositional characteristic of ordered microporous and mesoporous materials with inorganic hosts. L. B. McCusker, F. Liebau, G. Engelhardt, *Pure Appl. Chem.*, 73, pp. 381-394, 2001".

It has now been found that it is possible to carry out the catalytic rearrangement of cyclododecanone oxime to give lauryllactam in the gas phase over a zeolite.

SUMMARY OF THE INVENTION

The present invention relates to a process for the preparation of lauryllactam in which a Beckmann rearrangement of cyclododecanone oxime is carried out in the gas phase at a temperature of between 180 and 450° C. in the presence of a zeolite.

The zeolite is advantageously a zeolite exhibiting a pore distribution within the region of the wide pores (for example, pores with an opening delimited by rings comprising 12 tetrahedra).

According to a preferred embodiment of the invention, the process comprises the following stages:

a) the cyclododecanone oxime is either dissolved in a solvent chosen from alcohols and hydrocarbons or is in the molten state, b) the stream from stage a) is vaporized and brought into contact with the zeolite, optionally using a carrier gas, c) the lauryllactam is separated from the solvent, from the possible carrier gas and from the possible cyclododecanone oxime which has not been rearranged (converted).

According to another embodiment, the zeolite has aluminium and/or boron as framework heteroatom.

According to another embodiment, the zeolite is a zeolite which initially has aluminium and/or boron as framework heteroatom and which has been subjected to a dealumination/deboration treatment.

According to another embodiment, the zeolite is a β zeolite.

According to another embodiment, the zeolite is a β zeolite having aluminium and/or boron as framework heteroatom.

According to another embodiment, the zeolite is a β zeolite which initially has aluminium and/or boron as framework heteroatom and which has been subjected to a dealumination/deboration treatment.

In the text, the zeolite is sometimes denoted by the term "catalyst".

These operating conditions make it possible to reduce the accumulation of L12 (or of its derivatives) on the catalyst while minimizing the formation of coke, which would deactivate the catalyst. The reaction can be carried out at atmospheric pressure but, so as to operate in the gas state without reaching excessively high temperatures which would inevitably result in decomposition of the organic compounds and in irreversible deactivation of the catalyst, the reaction is preferably carried out under reduced pressure. It is recommended to periodically desorb the L12 and its derivatives adsorbed at the surface of the catalyst. This desorption is provided by treatments with air or under an inert gas at a temperature greater than the temperature of the zeolite during the Beckmann rearrangement. These treatments make it possible to avoid the conversion of the adsorbed products into coke, which would result in irreversible deactivation of the catalyst.

BRIEF DESCRIPTION OF THE DRAWINGS

FIG. 1 is a plot of the weight % of product adsorbed on the catalyst, Selectivity and Conversion from Test 4.

FIG. 2 charts the change in conversion and selectivity as a function of the successive test phases in the reaction from Test 7.

DETAILED DESCRIPTION OF THE INVENTION

As regards the temperature at which the rearrangement is carried out, operating at temperatures of less than 180° C. results in rapid and irreversible deactivation of the catalyst. On the other hand, temperatures of greater than 450° C. result in decomposition of the organic compounds with here again irreversible deactivation of the catalyst. Within the temperature range between 180 and 450° C., it is possible to synthesize lauryllactam with a selectivity generally of greater than 70%. In order also to obtain good conversion while protecting the catalyst from irreversible deactivation resulting from excessively high temperatures, it is recommended to operate within the range 225-400° C., the range 225-375° C. being particularly preferred.

As regards the operating pressure, in view of the fact that cyclodedecanone oxime and lauryllactam are difficult to vaporize and risk forming oligomers, indeed even coke, on the catalyst, it is preferable to operate at atmospheric pressure, indeed even under reduced pressure. Here again, it is necessary to find the best compromise, since a low pressure makes it possible to more easily desorb the organic compounds and thus to improve the selectivity. On the other hand, it limits the adsorption of the substrate on the catalyst and consequently reduces the conversion. In view of the temperature range selected, it is preferable to operate within the range 50-700 mbar absolute.

As regards the zeolite, these products are known per se and are available commercially. Use may be made, by way of examples, of a USY zeolite, a zeolite which has aluminium and/or boron as framework heteroatom, a zeolite which initially has aluminium and/or boron as framework heteroatom and which has been subjected to a dealumination/deboration treatment, a β zeolite, a β zeolite which has aluminium and/or boron as framework heteroatom or a β zeolite which initially has aluminium and/or boron as framework heteroatom and which has been subjected to a dealumination/deboration treatment. This dealumination/deboration treatment applied to zeolites or to β zeolites makes it possible to substantially improve the performance of the catalyst, in particular from the selectivity viewpoint. Numerous methods described in the literature exist for dealuminating, indeed even deborating, the zeolites; they are hydrothermal or chemical treatments of the zeolite. Mention may be made, without implied limitation, of the method disclosed in Patent EP 488 867. The advantage of the acidic treatment disclosed in this patent is that it makes it possible to retain the crystallinity of the zeolite. It is in particular highly appropriate for the dealumination/deboration of β zeolite. The operating conditions selected for this treatment make it possible to vary the extent of the dealumination/deboration of the zeolite and its effectiveness is measured by the Si/Al or Si/B atomic ratios of the solids obtained. The zeolite used can initially comprise boron. The treatment for removing a portion of the aluminium atoms of the zeolite also results in partial removal of the boron. The presence of residual boron does not affect the performance of the catalyst in terms of selectivity and even contributes to an improvement in the conversion. A zeolite initially comprising only boron as framework heteroatom results, after a deboration treatment, in a lower conversion; however, the selectivity still remains very good (greater than 90% under some operating conditions).

As regards the zeolites (optionally β zeolites) initially having the aluminium atom as framework heteroatom, a dealumination can be carried out which results in an Si/Al atomic ratio of greater than 50, advantageously of greater than 80 and preferably of greater than 150.

As regards the zeolites (optionally β zeolites) initially having the boron atom as framework heteroatom, a deboration can be carried out which results in an Si/B atomic ratio of greater than 20 and advantageously of greater than 40.

As regards the zeolites (optionally β zeolites) initially having the aluminium atom and the boron atom as framework heteroatom, a dealumination/deboration can be carried out which results in an Si/Al ratio of greater than 50 and an Si/B ratio of greater than 20, advantageously in an Si/Al ratio of greater than 150 and an Si/B ratio of greater than 30.

As regards the solvent, the cyclododecanone oxime can be dissolved in a solvent chosen from alcohols and hydrocarbons. It is recommended to choose the solvent in order to make it possible to dissolve the organic compounds and to have a stability of the solvent which is acceptable under the operating conditions selected for the reaction (temperature, zeolite, and the like). Generally, alcohols which may decompose in the presence of zeolites are markedly more stable in the presence of dealuminated and/or deboronated zeolites. Mention will be made, among the alcohols which can be used as solvent for cyclododecanone oxime, without implied limitation, of methanol, ethanol or isopropanol. Likewise, hydrocarbons can be used, alone or as mixtures, which makes it possible to have high dependence of the solubility of the products with the temperature, the latter property being important for the recovery and the purification of the final products. The use of isopropanol or of isopropanol/cyclohexane or ethanol/cyclohexane mixtures as solvent is particularly preferred. Furthermore, in order to increase the solubility of cyclododecanone oxime in the solvent and thus to increase the productive output of the rearrangement, it is possible to preheat the cyclododecanone oxime/solvent mixture before it is introduced into the reaction part.

As regards the carrier gas, mention may be made, by way of examples, of nitrogen, argon and helium.

As regards stage c), the separation can be carried out by any means.

As regards the "regeneration" of the catalyst, this term is used to denote the treatments which make possible the desorption of L12 and its derivatives adsorbed at the surface of the catalyst (of the zeolite). The catalysts (zeolites) and the operating conditions described above and in the examples result in good catalytic performances (selectivity and conversion) and make it possible to limit the accumulation of organic compounds on the catalyst. However, it is impossible to completely suppress this accumulation of organic products on the catalyst. For this reason, in order to improve the lifetime of the catalyst and to avoid irreversible deactivations, it is recommended to regenerate the catalyst as soon as a significant (10 to 20%) fall in the yield is observed. This regeneration is provided by flushing the catalyst and/or placing it under vacuum in the absence of the organic reactants. A temperature greater than the temperature at which the rearrangement reaction has been carried out is recommended. For this reason, the regeneration is carried out within a temperature range between 350 and 650° C. and more particularly between 400 and 600° C., the temperature range 450-590° C. being particularly preferred.

This regeneration can be carried out at atmospheric pressure or under reduced pressure. Likewise, it can be carried out while flushing with inert gases, such as nitrogen, or under oxygen or under a mixture of the two, such as air. The duration of the regeneration can be determined by monitoring the loss in weight of the catalyst due to the desorption of the organic compounds adsorbed on the catalyst. It generally requires several hours, if the phases of raising and lowering the temperature are taken into account. The regeneration can also be carried out under vacuum.

As regards the device in which the present rearrangement, as well as the preparation of the reactants and the recovery of the lauryllactam, are carried out, conventional equipment is used. More particularly, the rearrangement reaction over the zeolite can be carried out over "fixed bed", "fluid bed" or "moving bed" reactors. Due to the need to regularly regenerate the catalyst, it may be advantageous to use several reaction systems with a portion of them in production while the others are in the regeneration phase, and then vice versa.

EXAMPLES

Synthesis of β Zeolites

Synthesis of a β Zeolite with Aluminium as Framework Heteroatom: CAT 1

1.1 g of sodium hydroxide (Carlo Erba) are dissolved in 78.6 g of water and then 45 g of a 35% tetraethylammonium hydroxide (Aldrich) solution and 0.48 g of NaAlO$_2$ (Carlo Erba) are successively added with stirring. After dissolution, 18 g of Zeosil 175 MP silica are added, still with stirring. After a maturing stage with stirring at ambient temperature for 4 hours, the mixture is brought to a temperature of 150° C. under static conditions in an autoclave for 48 hours. The mixture obtained is filtered and then washing is carried out with water until a pH of 9.4 is obtained. The solid obtained is dried at 100° C. for 12 hours.

The elemental analysis of the dry solid indicates an Si/Al atomic ratio of 11.

Synthesis of a β Zeolite with Aluminium and Boron as Framework Heteroatoms: CAT 2

0.75 g of NaOH (Carlo Erba) is dissolved in 24 g of water and then 0.059 g of NaAlO$_2$ (Carlo Erba) and 0.492 g of Na$_2$B$_4$O$_7$ (Carlo Erba) are successively added with stirring. After dissolution, 45 g of a 35% tetraethylammonium hydroxide (Aldrich) solution and then 18 g of Zeosil 175 MP silica are added with stirring. After a maturing stage with stirring at ambient temperature for 4 hours, the mixture is brought to a temperature of 150° C. under static conditions in an autoclave for 48 hours. The mixture obtained is filtered, washing with water is then carried out until a pH of 9.1 is obtained and then centrifuging is carried out. The cake is finally dried at 100° C. for 14 hours.

The elemental analysis of the solid obtained indicates an Si/Al atomic ratio of 41 and an Si/B atomic ratio of 19.8.

Synthesis of a β Zeolite with Boron as Framework Heteroatom: CAT 3

3.48 g of boron hydroxide (B(OH)$_3$, Aldrich), 1.43 g of sodium hydroxide, 26.6 g of FK700 silica (Degussa) and 27.2 g of a 40% aqueous tetraethylammonium hydroxide (Fluka) solution are added to 183.6 ml of water and are kept stirred at ambient temperature overnight (13 h). 31.9 g of tetraethylammonium bromide are then added and the mixture is kept stirred for 5 h. The mixture is brought to 150° C. for 240 h under autogenous pressure in an autoclave equipped with a Teflon® lining. After filtration, the crystals obtained are calcined a first time at 400° C. under a stream of ammonia (3 l/h). After returning to ambient temperature, the solid is washed three times for 24 h with a 1M ammonium chloride solution. After filtration, the solid obtained is calcined at 400° C. under nitrogen.

The analysis of the solid thus synthesized displays an Si/B atomic ratio of 16.

Dealumination

Dealumination of CAT 1

In order to extract a portion of the aluminium, CAT 1, the synthesis of which is described above, is treated at 130° C. (reflux) in the presence of 70% nitric acid. Treatment at reflux for 5 hours, followed by washing with 17% nitric acid and then with water, results, after drying under air at 80° C., in a solid having an Si/Al atomic ratio of 150 (Catalyst CAT 1 dealumination Al1 (abbreviated to de Al1)). The solid obtained is subsequently calcined under air at 550° C. for 8 hours (rate of temperature rise: 2° C./minute).

An identical treatment but with a reflux stage lasting 6.5 hours results, after washing, drying and calcining, in a solid having an Si/Al atomic ratio of 180 (Catalyst CAT 1 dealumination Al2 (abbreviated to de Al2)).

Dealumination-deboration of CAT 2

In order to remove a portion of the framework heteroatoms of the catalyst CAT 2, this catalyst is treated at reflux (130° C.) of 70% nitric acid for 5 hours. After washing with 17% nitric acid and then with water, and drying, the solid is calcined under air at 550° C. for 8 hours (rate of temperature rise: 2° C./minute). A solid is thus obtained, the elemental analysis of which indicates an Si/Al atomic ratio of 170 and an Si/B atomic ratio of 37 (Catalyst CAT 2 dealuminated-deborated (abbreviated to de AlB1)).

Deboration of CAT 3

The catalyst CAT 3 is subjected to a treatment with an HCl solution (pH 6) at ambient temperature for one hour. After washing with water and then drying, the elemental analysis of the solid reveals an Si/B atomic ratio of 32 and an Si/Al atomic ratio of greater than 1500 (CAT 3 de B1).

Rearrangement Tests:

The cyclododecanone oxime, in solution in a solvent, is fed, via a pump, to an apparatus composed of a reaction system which can operate at atmospheric pressure or under pressure comprising a vaporization chamber and a reactor. The reduced pressure in the reaction part is provided by a vacuum pump equipped with a pressure gauge. Unless otherwise indicated, the charge of catalyst used in the fixed bed reactor is one gram. The combined reaction products are recovered in a liquid nitrogen trap.

Test 1: Test on the Catalyst CAT 1 (Non-dealuminated Catalyst)

For this test, the cyclododecanone oxime is dissolved in isopropanol at ambient temperature (3 g of oxime/100 g of isopropanol). The temperature in the catalytic bed is fixed at 325° C. and the operating pressure is set up at 50 mbar. Under these operating conditions, the cyclododecanone oxime/isopropanol mixture is injected accompanied by a carrier gas (3.5 Sl/h of nitrogen), which results in a space velocity of 0.3 g of oxime/g of catalyst.h. After starting up the plant (one hour), the crude reaction product is trapped for one hour. The analysis of this mixture leads to the following result: conversion of the oxime 85% and selectivity for lauryllactam 68%.

Test 2: Test on the catalyst CAT 1 de Al1

This Test 2 is carried out under operating conditions identical to those of Test 1, with the exception of the catalyst CAT 1, which is replaced by the catalyst CAT 1 de Al1. The analysis of the crude reaction product collected during the second hour of the test leads to the following result: conversion of the cyclododecanone oxime: 40%; selectivity for lauryllactam: 99%.

Test 3: Test on the Catalyst CAT 1 de Al2

This Test 3 is carried out under operating conditions identical to those of Test 1, with the exception of the catalyst CAT 1, which is replaced by the catalyst CAT 1 de Al2. The analysis of the crude reaction product collected during the second hour of the test leads to the following result: conversion of the cyclododecanone oxime: 48%; selectivity for lauryllactam: 99%.

Test 4: Test on the Catalyst CAT 2 de AlB1

This Test 4 is carried out under operating conditions identical to those of Test 1, with the exception of the catalyst CAT 1, which is replaced by the catalyst CAT 2 de AlB1. The analysis of the crude reaction product collected during the second hour of the test leads to the following result: conversion of the cyclododecanone oxime: 89%; selectivity for lauryllactam: 99.5%.

Test 5: Test on the Catalyst CAT 3 de B1

This Test 5 is carried out under operating conditions identical to those of Test 1, with the exception of the catalyst CAT 1, which is replaced by the catalyst CAT 3 de B1. The analysis of the crude reaction product collected during the second hour of the test leads to the following result: conversion of the cyclododecanone oxime: 28%; selectivity for lauryllactam: 92%.

The β zeolites used in these examples initially have aluminium or boron as framework heteroatoms. The best results are obtained with a zeolite initially comprising aluminium and boron which has been subjected to a dealumination/deboration treatment.

Test 6: Lifetime

For this test, the cyclododecanone oxime is dissolved in isopropanol at ambient temperature (3 g of oxime/100 g of isopropanol). This oxime/isopropanol mixture is injected into the vaporization chamber at a flow rate of 10 g/h. The catalyst used (3 g) is CAT 1 de Al2 and the temperature in the catalytic bed is set at 325° C. Furthermore, the operating pressure is set up at 50 mbar. After starting up the plant (one hour), the crude reaction product is trapped, weighed and analysed every hour. The change in the conversion and in the selectivity for L12 in the crude reaction product trapped at the outlet of the reactor and the material balance, which makes it possible to quantify the weight of product adsorbed on the catalyst, are illustrated in FIG. 1.

A balance over the first 12 hours of the test shows that, with regard to the 3.6 g of oxime introduced into the vaporization chamber, 3.36 g of products are recovered in the trap, the analysis of which shows that this mixture is very predominantly composed of L12 (>99%). The presence of traces of cyclododecanone is also observed. The missing product has remained adsorbed on the catalyst. Additional tests with regeneration show that it is possible, when the regeneration is carried out before a significant fall in the selectivity (regeneration before the selectivity is below 85%), to recover 96% of the product adsorbed on the catalyst and for this product to be very predominantly L12 (>95%). Consequently, over this period of 12 hours, a complete balance, including a "preventive regeneration" with nitrogen with trapping of the products desorbed, results in a yield of L12 of the order of 96%. Under such operating conditions, the productive output for L12 is of the order of 96 g/h.kg of catalyst.

The first 12 hours of the test are followed by a phase of 4 to 5 hours during which the selectivity falls slightly, accompanied by a gradual fall in the conversion down to approximately 80%. During this intermediate phase, there is no accumulation of product on the catalyst. The third phase (after testing for 16 hours) is illustrated by a more rapid deactivation of the catalyst, in particular of the conversion. There is again accumulation of organic compounds on the catalyst and the regeneration tests (under the conditions described below) undertaken over a catalyst at this stage show that it is not possible to completely desorb the accumulated products and irreversible deactivation of the catalyst is observed.

Test 7: Regeneration of the Catalyst

The same charge of catalyst (3 g) CAT 1 de Al2 was tested successively in reaction (P: 50 mbar, T=300° C., oxime introduced in solution in isopropanol, duration 2 hours, with trapping of the crude reaction product during the second hour)

and in regeneration (flushing under air at 550° C., total duration of the regeneration 12 hours (including the rise in the temperature to 550° C. and the fall to 300° C.), atmospheric pressure). The change in the conversion and in the selectivity (analysis based on the crude reaction product trapped) as a function of the successive phases of tests in reaction is reflected in FIG. 2.

After 8 tests in reaction, it is observed that, for all these tests, the cyclododecanone oxime is completely converted. The selectivity for L12, initially 95%, increases slightly to reach 98% during the eighth test in reaction. Due to the time necessary for the rise in the temperature to reach the stationary level of 550° C. and then the fall in the latter to return to the reaction temperature, it was not possible to shorten the regeneration phase. On the other hand, such a regeneration procedure (total duration 12 hours), applied to a catalyst which has operated in reaction for 12 hours, makes it possible to maintain the catalytic activity for the following reaction cycle.

The test was interrupted after 8 test/regeneration cycles without observing significant signs of deactivation of the catalyst.

On the basis of these results, it is thus possible to envisage a process with several reactors in parallel, some of which are in the reaction phase while others are in the regeneration phase.

Test 8: With a USY Zeolite (Other Family of Zeolites than β Zeolites)

The USY zeolite is sold by Grace; it has an Si/Al atomic ratio of 35. Test conditions identical to Test 1 above but using USY zeolite instead of β zeolite.

After starting up the plant (1 hour), the crude reaction product is trapped for 1 hour. The analysis of this mixture reveals a conversion of the oxime of 74% and a selectivity for L12 of 75%.

The invention claimed is:

1. A process for the preparation of lauryllactam comprising carrying out a Beckmann rearrangement of cyclododecanone oxime in the gas phase at a temperature of between 180 and 450° C. in the presence of a microporous zeolite material having a three-dimensional inorganic main structure composed of tetrahedra connected via a common edge, wherein said zeolite is a zeolite exhibiting a pore distribution within the region of the wide pores having an opening delimited by rings comprising 12 tetrahedra.

2. The process according to claim 1, wherein:
a) the cyclododecanone oxime is either dissolved in a solvent chosen from alcohols, hydrocarbons, and mixtures of alcohols and hydrocarbons, or is in the molten state, to form a cyclododecanone stream;
b) the cyclodecanone stream from step a) is vaporized and brought into contact with the zeolite, optionally using a carrier gas;
c) the lauryllactam is separated from the solvent, from the optional carrier gas and from any cyclododecanone oxime which has not been converted.

3. The process according to claim 1, wherein the temperature of the rearrangement is between 225 and 400° C.

4. The process according to claim 3, wherein the temperature is between 225 and 375° C.

5. The process according to claim 1, wherein the rearrangement is carried out at a pressure of between 50 and 700 mbar absolute.

6. The process according to claim 1, wherein the zeolite is a USY zeolite.

7. The process according to claim 1, in which the zeolite is selected from the group of zeolites consisting of a zeolite which has aluminium and/or boron as framework heteroatom, a zeolite which initially has aluminium and/or boron as framework heteroatom and which has been subjected to a dealumination/deboration treatment, a β zeolite, a β zeolite which has aluminium and/or boron as framework heteroatom, and a β zeolite which initially has aluminium and/or boron as framework heteroatom and which has been subjected to a dealumination/deboration treatment.

8. The process according to claim 7, wherein the zeolite is a zeolite which initially has aluminium and/or boron as framework heteroatom and which has been subjected to a dealumination/deboration treatment.

9. The process according to claim 8, wherein the zeolite is a β zeolite which initially has aluminium and/or boron as framework heteroatom and which has been subjected to a dealumination/deboration treatment.

10. The process according to claim 9, in which the β zeolite which initially has aluminium as framework heteroatom is subjected to a dealumination resulting in an Si/Al atomic ratio of greater than 50.

11. The process according to claim 10, in which the β zeolite which initially has the aluminium atom as framework heteroatom is subjected to a dealumination resulting in an Si/Al atomic ratio of greater than 80.

12. The process according to claim 11, in which the β zeolite which initially has the aluminium atom as framework heteroatom is subjected to a dealumination resulting in an Si/Al atomic ratio of greater than 150.

13. The process according to claim 9, in which the β zeolite which initially has the boron atom as framework heteroatom is subjected to a deboration resulting in an Si/B atomic ratio of greater than 20.

14. The process according to claim 13, in which the β zeolite which initially has the boron atom as framework heteroatom is subjected to a deboration resulting in an Si/B atomic ratio of greater than 40.

15. The process according to claim 8, in which the β zeolite which initially has the aluminium atom and the boron atom as framework heteroatom is subjected to a dealumination/deboration resulting in an Si/Al ratio of greater than 50 and an Si/B ratio of greater than 20.

16. The process according to claim 15, in which the β zeolite which initially has the aluminium atom and the boron atom as framework heteroatom is subjected to a dealumination/deboration resulting in an Si/Al ratio of greater than 150 and an Si/B ratio of greater than 30.

17. The process according to claim 2, wherein the cyclododecanone oxime is introduced in the molten state.

18. The process according to claim 2, wherein the cyclododecanone oxime is dissolved in a solvent chosen from alcohols and hydrocarbons and wherein the alcohol is chosen from methanol, ethanol or isopropanol.

19. The process according to claim 2, wherein the solvent is chosen from isopropanol/cyclohexane and ethanol/cyclohexane mixtures.

20. The process according to claim 1, wherein the zeolite is regenerated.

21. The process according to claim 20, wherein the zeolite is regenerated as soon as a fall in the yield of between 10 and 20% is observed.

* * * * *